(12) United States Patent
Hill et al.

(10) Patent No.: US 10,385,332 B2
(45) Date of Patent: Aug. 20, 2019

(54) TWO-HYBRID BASED SCREEN TO IDENTIFY DISRUPTIVE RESIDUES AT MULTIPLE PROTEIN INTERFACES

(71) Applicant: THE JOHNS HOPKINS UNIVERSITY, Baltimore, MD (US)

(72) Inventors: R. Blake Hill, Baltimore, MD (US); Cara Marie Manlandro, Derwood, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/011,729

(22) Filed: Feb. 1, 2016

(65) Prior Publication Data
US 2017/0022494 A1    Jan. 26, 2017

Related U.S. Application Data

(63) Continuation of application No. 13/326,788, filed on Dec. 15, 2011, now Pat. No. 9,249,410.

(60) Provisional application No. 61/423,210, filed on Dec. 15, 2010.

(51) Int. Cl.
    *C12N 15/10*    (2006.01)
(52) U.S. Cl.
    CPC ................................ *C12N 15/1055* (2013.01)
(58) Field of Classification Search
    None
    See application file for complete search history.

(56) References Cited

U.S. PATENT DOCUMENTS 8,399,201 B2 *  3/2013  Qin ..................... C07K 14/705
                                                       435/7.1

OTHER PUBLICATIONS

Zhang et al., Proc. Nat. Acad. Sci. USA, 104:18256-18530, 2007 (Year: 2007).*
Wells, J., et al., "Reaching for high-hanging fruit in drug discovery at protein-protein interfaces", Nature vol. 450, 1001-1009 (2007).
Mandell, D., et al., "Computer-aided design of functional protein interactions", Nature Chemical Biology, vol. 5, No. 11, pp. 797-807 (2009).
Fields, S., et al., "A Novel Genetic System to Detect Protein Protein Interactions", Nature vol. 340, pp. 245-246 (1989).
Chien, C., et al., "The 2-Hybrid System—a Method to Identify and Clone Genes for Proteins that Interact with a Protein of Interest", Proc. Natl. Acad. Sci. U. S. A., vol. 88, pp. 9578-9582 (1991).
Uetz, P., et al., "A comprehensive analysis of protein-protein interactions in *Saccharomyces cerevisiae*" Nature, vol. 403, pp. 623-627 (2000).
Ito, T., et al., "A comprehensive two-hybrid analysis to explore the yeast protein interactome" Proc. Natl. Acad. Sci. U. S. A., vol. 98, No. 8, pp. 4569-4574 (2001).
Stelzl, U., et al., "A human protein-protein interaction network: A resource for annotating the proteome", Cell, vol. 122, pp. 957-968 (2005).
Rual, J., et al., "Towards a proteome-scale map of the human protein-protein interaction network", Nature, vol. 437, pp. 1173-1178 (2005).
Walhout, A., et al., "Yeast two-hybrid systems and protein interaction mapping projects for yeast and worm", Yeast, vol. 17, pp. 88-94 (2000).
Walhout, A., et al., "High-throughput yeast two-hybrid assays for large-scale protein interaction manning" Methods, vol. 24, pp. 297-306 (2001).
Gyuris, J., et al., "Cdi1, a Human G1-Phase and S-Phase Protein Phosphatase that Associates with Cdk2" Cell, vol. 75, pp. 791-803 (1993).
Finley, R., et al., "Interaction Mating Reveals Binary and Ternary Connections between *Drosophila* Cell-Cycle Regulators" Proc. Natl. Acad. Sci. U. S. A., vol. 91, pp. 12980-12984 (1994).
Bendixen, C., et al., "A Yeast Mating-Selection Scheme for Detection of Protein-Protein Interactions" Nucleic Acids Res. vol. 22, No. 9, pp. 1778-1779 (1994).
Fromont-Racine, M., et al., "Genome-wide protein interaction screens reveal functional networks involving Sm-like proteins", Yeast, vol. 17, pp. 95-110 (2000).
Parrish, J., et al., "Yeast two-hybrid contributions to interactome mapping", Curr. Opin. Biotechnol. vol. 17, pp. 387-393 (2006).
Videl, M., et al., "Reverse two-hybrid and one-hybrid systems to detect dissociation of protein-protein and DNA-protein interactions", Proc. Natl. Acad. Sci. U. S. A., vol. 93, pp. 10315-10320 (1996).
Videl, M., et al., "Genetic characterization of a mammalian protein-protein interaction domain by using a yeast reverse two-hybrid system", Proc. Natl. Acad. Sci. U. S. A., vol. 93, pp. 10321-10326 (1996).
Clackson, T., et al., "A Hot-Spot of Binding-Energy in a Hormone-Receptor Interface" Science, vol. 267, No. 267, pp. 383-386 (1995).

(Continued)

*Primary Examiner* — Nancy A Treptow
(74) *Attorney, Agent, or Firm* — Johns Hopkins Technology Ventures

(57) ABSTRACT

The present invention is based, at least in part, on the development of a mating-based yeast two-hybrid screen that allows simultaneous screening for mutations that disrupt yeast two-hybrid interactions between a protein and multiple interacting partners. By coupling PCR mutagenesis and homologous recombination/gapped plasmid repair with a mating-based assay, the present invention allows screening for unique mutations that disrupt interaction with one partner, but not others. It also allows identification of specific mutations that may lie at protein-protein interfaces common to two or more partners, without employing multiple rounds of screening. In addition to screening against multiple interacting partners, the present invention removes the need for a two-step selection because truncations, frameshifts, or any mutations that affect folding are eliminated as disruptions that affect all protein partners. The methods of the present invention are named "Hotspot" because of its ability to identify "hotspot residues" in protein-protein interfaces.

4 Claims, 11 Drawing Sheets

(56) References Cited

OTHER PUBLICATIONS

Bonsor, D., et al., "Dissecting Protein-Protein Interactions Using Directed Evolution", Biochemistry, vol. 50, pp. 2394-2402 (2011).
Keskin, O., et al., "Hot regions in protein-protein interactions: The organization and contribution of structurally conserved hot spot residues", J. Mol. Biol., vol. 345, pp. 1281-1294 (2005).
Fleishman, S., et al., "Hotspot-Centric De Novo Design of Protein Binders" J. Mol. Biol., vol. 413, No. 5, pp. 1047-1062 (2011).

* cited by examiner

| Bait | Prey | + Histidine | - Histidine |
|---|---|---|---|
| Empty | Empty | | |
| Fis1ΔTM | Empty | | |
| Fis1ΔTM | Fis1ΔTM | | |
| Fis1ΔTM 17 | Empty | | |
| Fis1ΔTM 17 | Fis1ΔTM | | |
| Fis1ΔTM 17 | Fis1ΔTM 17 | | |
| Dnm1 | Empty | | |
| Dnm1 | Fis1ΔTM | | |
| Dnm1 | Fis1ΔTM 17 | | |
| Mdv1 | Empty | | |
| Mdv1 | Fis1ΔTM | | |
| Mdv1 | Fis1ΔTM 17 | | |

FIG. 7

| Growth Assay Phenotype | Number of Mutants |
|---|---|
| No growth (Functional Fission) | 57 |
| Slight growth (Functional Fission) | 58 |
| Intermediate growth (Non-functional Fission) | 46 |
| Robust growth (Non-functional Fission) | 50 |

FIG. 9

| Class | Disrupted Yeast 2-Hybrid | | | # clones | average # changes |
|---|---|---|---|---|---|
| | Fis1 | Dnm1 | Mdv1 | | |
| 1 | + | | | 28 | 3 |
| 2 | | + | | 32 | 3 |
| 3 | | | + | 40 | 3 |
| 4 | + | + | | 23 | 4 |
| 5 | + | | + | 20 | 5 |
| 6 | | + | + | 24 | 5 |
| 7 | | | | 80 | 2 |
| 8 | + | + | + | 50* | 6 |

FIG. 10

|  | Number of Clones | | | |
|---|---|---|---|---|
|  | No Disruptions | Single Disruptions | Double Disruptions | Triple Disruptions |
| Frameshift Mutations | 1 | 1 | 2 | 24 |
| Premature Stop Codons | 0 | 1 | 0 | 17 |
| Full-Length Constructs | 49 | 98 | 39 | 9 |
| Total Clones Sequenced | 50 | 100 | 41 | 50 |

FIG. 11

TWO-HYBRID BASED SCREEN TO IDENTIFY DISRUPTIVE RESIDUES AT MULTIPLE PROTEIN INTERFACES

CROSS-REFERENCE TO RELATED APPLICATIONS

This application is a Continuation of U.S. application Ser. No. 13/326,788, filed Dec. 15, 2011, now U.S. Pat. No. 9,249,410, issued Feb. 2, 2016, which claims the benefit of U.S. Provisional Application No. 61/423,210, filed Dec. 15, 2010, the content of each of the aforementioned applications is herein incorporated by reference in their entirety.

STATEMENT OF GOVERNMENTAL INTEREST

This invention was made with government support under grant number GM067180 awarded by the National Institutes of Health. The government has certain rights in this invention.

FIELD OF THE INVENTION

The present invention generally relates to the study of protein-protein interactions, and particularly to yeast two-hybrid systems for identifying amino acids involved in protein-protein interactions.

BACKGROUND OF THE INVENTION

Specific protein-protein interactions are essential to nearly every biological process. Defining how specific interactions are made is critical for a full understanding of the biological system governed by the interacting proteins. Yeast two-hybrid analysis is a routine and powerful assay for examining protein-protein interactions that has been adapted to high-throughput screening (Fields, S. & Song, O. K., 340 NATURE 245-46 (1989), Chien et al., 88 PROC. NATL. ACAD. SCI. U.S.A. 9578-82 (1991)). In fact, large-scale yeast two-hybrid screening has been utilized to collect much of the binary protein interaction data available to date (Uetz et al., 403 NATURE 623-27 (2000), Ito et al., 98 PROC. NATL. ACAD. SCI. U.S.A. 4569-74 (2001), Stelzl et al., 122 CELL 957-68 (2005), Rual et al., 437 NATURE 1173-78 (2005), Walhout et al., 17 YEAST 88-94 (2000)). However, such large-scale yeast two-hybrid screens face numerous challenges, including strategies for cloning numerous genes into yeast two-hybrid vectors for expressing DNA-binding domain ("bait") and activation domain ("prey") fusions in yeast. Conventional techniques involving individual restriction digests and ligations for cloning genes into appropriate expression vectors can be impractical and expensive when dealing with thousands of genes. Several alternative systems for cloning yeast two-hybrid constructs based on DNA homologous recombination reactions have been described to date (Uetz et al., 2000, Walhout et al., 2000). Even though these techniques eliminate the need for restriction enzymes and ligases, they still require thousands of yeast transformations to generate a library of activation-domain fusion constructs (Uetz et al., 2000, Walhout et al., 2000).

The development of mating-based screens has facilitated the conversion of yeast two-hybrid from a directed, small-scale assay to a high-throughput one (Gyuris et al., 75 CELL 791-803 (1993), Finley, R. L. & Brent, R., 91 PROC. NATL. ACAD. SCI. U.S.A. 12980-12984 (1994), Bendixen et al., 22 NUCLEIC ACIDS RES. 1778-79 (1994), Fromont-Racine et al., 17 YEAST 95-110 (2000)). Mating-based screens rely on haploid yeast having two mating types, MATa and MATα, which fuse to form diploids (Herskowitz et al., 57 MICROBIOL. REV. 536 (1988)). In these assays, DNA-binding and activation-tagged proteins are expressed in different haploid strains and are brought together through mating (Gyuris et al., 1993). Large numbers of individual protein-protein interactions can then be tested (Gyuris et al., 1993, Finley and Brent, 1994, Fromont-Racine et al., 1997, Walhout A. J. M. & Vidal, M., 24 METHODS 297-306 (2001)). However, establishing efficient strategies to mate large sets of bait and prey yeast strains to sample all possible combinations of interactions has also proven difficult (Uetz et al., 2000, Parrish et al., 17(4) CURR. OPIN. BIOTECHNOL. 387-93 (2006)).

Another limitation of the classic yeast two-hybrid system is simultaneous detection of multiple protein-protein interactions. Ternary-protein complexes in which a protein requires interaction with a second protein in order to bind a third protein, and where a third protein only binds to a composite site formed by the association of the first and second proteins, can be analyzed using a yeast "three-hybrid system" (Zhang, Y. & Chan, D. C., 104 PROC. NATL. ACAD. SCI. U.S.A. 18526-18530 (2007)). However, assays for simultaneous screening of multiple interacting partners have yet to be described, and current technology requires multiple rounds of screening (Fromont-Racine et al., 1997).

Yeast two-hybrid assays have also been useful in mapping binary protein-protein interfaces (Lehming et al., 92 PROC. NATL. ACAD. SCI. U.S.A. 92, 10242-10246 (1995), Steffan et al., 18 MOL. CELL. BIOL. 3752-61 (1998), Vidal et al., 93 PROC. NATL. ACAD. SCI. U.S.A. 93, 10315-10320 (1996)). These assays often utilize PCR-based random mutagenesis followed by homologous recombination and gapped plasmid repair to construct a library of mutated proteins to screen for disruption of interaction with its binding partner (Lehming et al., 1995, Steffan et al., 1998). However, a common issue with this type of approach is the generation of uninformative mutations, such as truncations, frameshifts, or any mutations that affect the stability, processing or folding of the protein. To eliminate isolation of these trivial results, a "reverse yeast two-hybrid" system was developed (Vidal et al., 93 PROC. NATL. ACAD. SCI. U.S.A. 93, 10321-10326 (1996)) to include a two-step selection process. The first step is a negative selection for mutations that impair a protein-protein interaction and the second step is a positive selection for a subset of those mutations that maintain expression of full-length stable proteins (Vidal et al., 93 PROC. NATL. ACAD. SCI. U.S.A. 93, 10321-10326 (1996)). While this two-step selection accomplishes both identification of disruptive mutations and elimination of trivial mutations, it can only be used to study the interactions of two proteins partners.

To date, mutagenesis-based yeast two-hybrid screens have only been utilized to examine the interactions of binary protein-protein interactions, and have not been extended to the analysis of multiple interacting partners.

SUMMARY OF THE INVENTION

The present invention generally relates to the study of protein-protein interactions, and particularly to yeast two-hybrid systems for identifying amino acids involved in protein-protein interactions. More specifically, the present invention is based, at least in part, on the development of a mating-based yeast two-hybrid screen that allows simultaneous screening for mutations that disrupt yeast two-hybrid interactions between a protein and multiple interacting partners. By coupling PCR mutagenesis and homologous recombination/gapped plasmid repair with a mating-based assay, the present invention allows screening for unique mutations that disrupt interaction with one partner, but not others. It also allows identification of specific mutations that may lie at protein-protein interfaces common to two or more partners, without employing multiple rounds of screening. In addition to screening against multiple interacting partners, the present invention removes the need for a two-step selection because truncations, frameshifts, or any mutations that affect folding are eliminated as disruptions that affect all protein partners. The methods of the present invention are named "Hotspot" because of its ability to identify "hotspot residues" in protein-protein interfaces (Clackson, T. & Wells, J., 267 SCIENCE 383-86 (1995)). In one embodiment, the Hotspot assay is applied to the protein Fis1, which is involved in mitochondrial fission, and its interactions with 3 binding partnersitself, Dnm1 and Mdv1 and identified previously unknown interaction interfaces in these proteins.

Accordingly, in one aspect, the present invention provides methods and compositions useful to study interactions between a protein and its multiple interacting partners. In one embodiment, a method for identifying a protein interaction domain of a target protein using a yeast two-hybrid system comprises the steps of (a) mating a first haploid yeast cell expressing a mutant target protein with (i) a second haploid yeast cell expressing a first interacting partner of the target protein, wherein the mutant target protein is fused to a transcription factor activating domain and the first interacting partner of the target protein is fused to the DNA binding domain of the same transcription factor; and (ii) a third haploid yeast cell expressing a second interacting partner of the target protein, wherein the second interacting partner of the target protein is fused to the DNA binding domain of the same transcription factor; (b) selecting for diploid mated cells expressing both the mutant target protein and the first or second interacting partner; and selecting for yeast two-hybrid interactions between the mutant target protein and the first interacting partner or the second interacting partner, wherein a disruption of the yeast two-hybrid interaction indicates that the mutated amino acids of the target protein comprise a protein interaction domain. In another embodiment, steps (a)(i) and (a)(ii) are carried out simultaneously. In a further embodiment, steps (b) and (c) are carried out simultaneously using the replica plating technique. In yet another embodiment, steps (a)(i) and (a)(ii) are carried out simultaneously and wherein steps (b) and (c) are carried out simultaneously.

In a specific embodiment, the first haploid yeast cell is of mating type a and the second and third haploid yeast cells are of mating type α. In another embodiment, the mutant target protein comprises about 2 to about 5 amino acids that are mutated relative to the wild type target protein. In a further embodiment, the method further comprises mating the first haploid yeast cell expressing a mutant target protein with a fourth haploid yeast cell expressing a third interacting partner of the target protein, wherein the third interacting partner of the target protein is fused to the DNA binding domain of the same transcription factor.

The present invention also provides a method for using a yeast two-hybrid system to identify amino acid residues of a target protein that interact with interacting partners of the target protein comprising the steps of (a) providing a first haploid yeast cell expressing a mutant target protein fused to either an activation domain or a DNA binding domain of a transcription factor; (b) providing at least two haploid yeast cells expressing different interacting partners of the mutant target protein, wherein each interacting partner is fused to either (i) an activation domain of a transcription factor if the mutant target protein of step (a) is fused to the DNA binding domain of the transcription factor or (ii) a DNA binding domain of a transcription factor if the mutant target protein of step (a) is fused to the activation domain of the transcription factor; (c) mating the first haploid yeast cell separately with each of the at least two haploid yeast cells; (d) replica plating the mating reactions to select for mated diploid yeast cells; and (e) replica plating the mating reactions to select for yeast two-hybrid interactions, wherein a disruption of the yeast two-hybrid interaction indicates that the mutated amino acids of the target protein interact with an interacting partner of the target protein. In certain embodiments, the first haploid yeast cell is of mating type a and the at least two haploid yeast cells expressing different interacting partners of the mutant target protein are of mating type α. In specific embodiments, the mutant target protein comprises about 2 to about 5 amino acids that are mutated relative to the wild type target protein.

In other embodiments, a method for using a yeast two-hybrid system to identify amino acid residues of a target protein that interact with interacting partners of the target protein comprises the steps of (a) separately mating a first haploid yeast cell expressing a mutant target protein with at least two haploid yeast cells expressing different interacting partners of the target protein, wherein the mutant target protein is fused to a transcription factor activating domain and the interacting partners of the target protein are fused to the DNA binding domain of the same transcription factor; (b) selecting for diploid mated cells expressing both the mutant target protein and the first or second interacting partner, wherein the transcription factor activating domain and the DNA binding domain activate transcription of a reporter gene when the target protein and the interacting partner fusion proteins interact; and (c) selecting for yeast two-hybrid interactions between the mutant target protein and the first interacting partner or the second interacting partner, wherein a disruption of the yeast two-hybrid interaction indicates that the mutated amino acids of the target protein interact with an interacting partner of the target protein. In specific embodiments, the first haploid yeast cell is of mating type a and the at least two haploid yeast cells expressing different interacting partners of the target protein are of mating type α. In particular embodiments, the mutant target protein comprises about 2 to about 5 amino acids that are mutated relative to the wild type target protein.

In an alternative embodiment, a method for using a yeast two-hybrid system to identify amino acid residues of a target protein that interact with interacting partners of the target protein comprises the steps of (a) mating a first haploid yeast cell expressing a prey mutant target protein with (i) a second haploid yeast cell expressing a first bait interacting partner of the target protein, wherein the mutant target protein is fused to a transcription factor activating domain and the first bait interacting partner of the target protein is fused to the DNA binding domain of the same transcription factor; and (ii) a third haploid yeast cell expressing a second bait interacting partner of the target protein, wherein the second bait interacting partner of the target protein is fused to the DNA binding domain of the same transcription factor; (b) selecting for diploid mated cells expressing both the prey mutant target protein and the first bait or second bait interacting partner; and (c) selecting fix yeast two-hybrid interactions between the prey mutant target protein and the first bait interacting partner or the second bait interacting partner, wherein a disruption of the yeast two-hybrid interaction indicates that the mutated amino acids of the target protein interact with an interacting partner of the target protein. In specific embodiments, the first haploid yeast cell is of mating type a and the second and third haploid yeast cells are of mating type α. In other embodiments, the prey mutant target protein comprises about 2 to about 5 amino acids that are mutated relative to the wild type target protein.

In a specific embodiment, the present invention provides a method for identifying amino acid residues of a hub protein that are involved in protein-protein interaction comprising the steps of (a) providing a first haploid yeast cell of mating type a that expresses a mutant hub protein fused to either an activation domain or a DNA binding domain of a transcription factor; (b) providing at least two haploid yeast cells of mating type α that expresses different interacting partners of the mutant hub protein, wherein each interacting partner is fused to either (i) an activation domain of a transcription factor if the mutant hub protein of step (a) is fused to the DNA binding domain of the transcription factor or (ii) a DNA binding domain of a transcription factor if the mutant huh protein of step (a) is fused to the activation domain of the transcription factor; (c) mating the first haploid yeast cell separately with each of the at least two haploid yeast cells; (d) replica plating the mating reactions to select for mated diploid yeast cells; and (e) replica plating the mating reactions to select for two-hybrid interactions, wherein a single disruption of the yeast two-hybrid interaction indicates that the mutated amino acids of the hub protein are involved at a target protein interface with an interacting partner, wherein a double disruption of the yeast two-hybrid interaction indicates that the mutated amino acids of the hub protein are involved at a target protein interface with two interacting partners, and wherein a disruption of the two-hybrid interaction in all selection reactions indicates that the disruption is due to a mutation not relevant to a disruption of the interaction between the hub protein and the interacting partners. In certain embodiments, the mutant target protein comprises about 2 to about 5 amino acids that are mutated relative to the wild type target protein.

In another aspect, the present invention provides methods and compositions using a co-transformation approach to study a target protein's interaction with multiple interacting partners. More specifically, a method for using a two-hybrid system to identify amino acid residues of a target protein that interact with interacting partners of the target protein comprising the steps of (a) co-transforming a plurality of eukaryotic cells with (i) expression vectors expressing a library of mutant target proteins and (ii) expression vectors expressing the interacting partners of the target protein, wherein each transformation reaction comprises a mutant target protein and an interacting partner; and (b) selecting for two-hybrid interactions between the mutant target protein and the interacting partner, wherein a disruption of the two-hybrid interaction indicates that the mutated amino acids of the target protein interact with the interacting partner. In a specific embodiment, the eukaryotic cell is yeast. In another embodiment, the eukaryotic cell is mammalian. In particular embodiments, the mutant target proteins are fused to an activation domain of a transcription factor and the interacting partners are fused to a DNA binding domain of the transcription factor.

In another specific embodiment, a method for using a two-hybrid system to identify amino acid residues of a target protein that interact with interacting partners of the target protein comprises the steps of (a) co-transforming eukaryotic cells with (i) an expression vector encoding a mutant target protein and (ii) an expression vector encoding an interacting partner that interacts with the target protein; (b) repeating step (a) with expression vectors that encode N−1 of the remaining interacting partners that interact with the target protein, wherein N is the total number of interacting partners that interact with the target protein; (c) repeating steps (a) and (b) with expression vectors encoding other mutant target proteins; and (d) selecting for two-hybrid interactions, wherein a disruption of the two hybrid interaction in a selection reaction indicates that the mutated amino acids of the target protein interact with the interacting partner expressed in the selection reaction. In a further embodiment, a disruption of the two hybrid interaction in all N selection reactions for a mutated target protein indicates that the disruption is due to a mutation not relevant to a disruption of the interaction between the mutant target protein and the interacting partner. In a more specific embodiment, a mutation not relevant to a disruption of the interaction between the mutant target protein and the interacting partner comprises a frameshift mutation, a premature stop codon, or a mutation that unfolds the mutant target protein. In another embodiment, the eukaryotic cell is yeast. In an alternative embodiment, the eukaryotic cell is mammalian.

In yet another embodiment, the present invention provides a method for using a yeast two-hybrid system to identify amino acid residues of a target protein that interact with interacting partners of the target protein comprising the steps of (a) providing a first haploid yeast cell of mating type a that expresses a mutant target protein fused to either an activation domain or a DNA binding domain of a transcription factor; (b) providing N haploid yeast cells of mating type α that express N interacting partners of the mutant target protein, wherein N equals the number of interacting partners of the target protein, and wherein each interacting partner is fused to either (i) an activation domain of a transcription factor if the mutant target protein of step (a) is fused to the DNA binding domain of the transcription factor or (ii) a DNA binding domain of a transcription factor if the mutant target protein of step (a) is fused to the activation domain of the transcription factor; (c) mating the first haploid yeast cell separately with each of the N haploid yeast cells; (d) replica plating the mating reactions to select for mated diploid yeast cells; and (e) replica plating the mating reactions to select for two-hybrid interactions, wherein a single disruption of the yeast two-hybrid interaction indicates that the mutated amino acids of the target protein are involved at a target protein interface with an interacting partner, wherein a double disruption of the yeast two-hybrid interaction indicates that the mutated amino acids of the target protein are involved at a target protein interface with two interacting partners, and wherein a disruption of the two-hybrid interaction in all N selection reactions indicates that the disruption is due to a mutation not relevant to a disruption of the interaction between the target protein and the interacting partners.

Accordingly, the methods and compositions of the present invention can be used to study proteins that interact with multiple partners. In certain embodiments, the target protein is a hub protein. Signalling hub proteins that can be studied using the present invention include, but are not limited to, PDK1, Wnt, Beta-catenin, Src, Akt, Erk-1, MAPK, CDK, PTEN, PGCa, Rck1, Tra1, DISC1, Grb2, AP2, Clathrin, p53, and NFkB. Any of the G-protein coupled receptors (GPCR) can be studied as well. Small GTPas signaling (Ras-GRPase and Rho-GTpase), as well as cytokine signaling including cytokines that are involved in the Stat pathway can be studied using the methods and compositions of the present invention. Generally, the present invention can be used to study an "interactome." The most interactive families that make up the interactome core include P-loop containing nucleotide triphosphate hydrolases, immunoglobulins, E set domains, trypsin-like serin proteases, winged helix DNA-binding domain, nucleic acid-binding domains, (Trans)glycosidases, cytochrome c, 4Fe-4S ferredoxins, EGH/Laminin, EF-hand, NAD(P)-binding Rossmann-fold domains, FAD/NAD(p)-binding domain, eupredoxins, ribosomal protein S5 domain 2-like, protein kinase-like (PK-like), 2Fe-2S ferredoxin-like, ARM repeat, galactose-binding domain-like, and the actin-like ATPase domain.

BRIEF DESCRIPTION OF THE FIGURES

FIG. 6C shows that the difference in 3HA-Mdv1 co-immunoprecipitation was not due to differences in expression levels, as determined by TCA precipitation of yeast whole-cell lysate, followed by an anti-HA Western blot.

FIG. 7 shows that $\Delta N_{16}Fis1\Delta TM$ interacts strongly with $\Delta N_{16}Fis1\Delta TM$. Dnm1, and Mdv1 by yeast two-hybrid. Yeast two-hybrid assays were performed using the HIS3 reporter. Cells with the indicated bait and prey constructs were grown overnight in selective media, pelleted by centrifugation, and subjected to 10-fold serial dilutions in water, with a starting concentration of 1 $OD_{600}$/ml. Cells were spotted onto media containing histidine (growth control) and media lacking histidine to select for yeast two-hybrid interactions and plates were photographed after incubation for 3 days at 30° C.

FIG. 9 shows that Fis1 mutant alleles that disrupt Fis1-Fis1, Fis1-Dnm1 and Fis1-Mdv1 interactions in Hotspot are deficient in mitochondrial fission in vivo. Each mutant allele isolated by Hotspot as a Fis1-Mdv1, Fis1-Dnm1, or Fis1-Fis1 selective disruption was subcloned into a galactose-inducible Fis1 plasmid, and tested for its ability to restore functional fission to fis1Δfzo1Δ yeast. Cells were grown overnight in selective media, collected by centrifugation, resuspended to a concentration of 1 $OD_{600}$/ml, and subjected to 10-fold serial dilutions in water. Cells were plated onto YP+Dextrose as a growth control and YP+Glycerol to select for restoration of functional mitochondrial fission. Plates were photographed alter incubation at 30° C. for 5 days. This experiment was repeated twice with similar results.

FIG. 10 is a table summarizing the Hotspot screen with Fis1, Dnm1 and Mdv1. Mutant alleles in each of the eight possible classes of disruptions (3 single, 3 double, 1 zero, and 1 triple) were identified. The total number of clones sequenced to date is 297 out of 3008 visually screened colonies. The average number of amino acid changes per allele is given in the last column. For triple disruptions, 50 clones were sequenced, but the number of amino acid changes was calculated only for clones that were full-length transcripts (denoted by an asterisk*).

FIG. 11 is a table summarizing the disruptions in Hotspot analysis of Fis1, Dnm1, and Mdv1. Note that only 2.6% of alleles identified derived from frameshift mutations or premature stop codons, which occurred in the last 18 nt of the Fis1 gene.

DETAILED DESCRIPTION OF THE INVENTION

Figure 1:
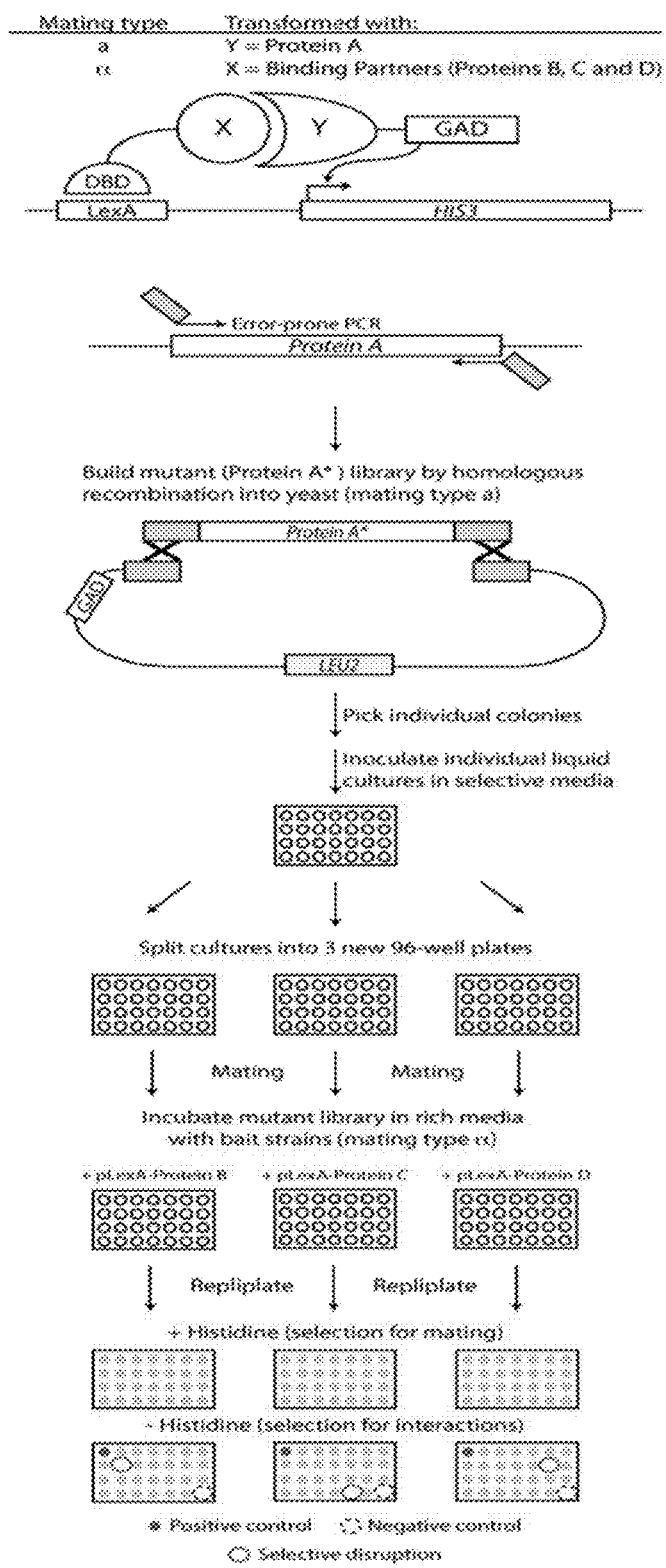
FIG. 1 is a schematic representation of the Hotspot screen for simultaneously identifying disruptive residues in one protein that shows yeast two-hybrid interactions with multiple protein partners. In this approach, the present inventors screened for disruptions of yeast two-hybrid interactions between a "hub protein" (Protein A) and "spoke proteins" (Proteins B, C, D, and so on). A mutant library of Protein A was randomly generated using error-prone PCR. This library was transformed into yeast with mating type a by homologous recombination. Individual colonies represent distinct mutant alleles of Protein A and were then mated with Proteins B, C, and D in the bait strains of matin type α. Mating ensures proper plasmid transfer and the subsequent replica plating ("replating") allows for selection of disruptive interactions simultaneously. While this approach was demonstrated here for three interacting partners, it could be extended for multiple interactions. Note that Hotspot is designed to serve as its own internal control by immediately identifying disruptions caused by trivial reasons, since frameshift mutations, premature stop codons, and mutations that unfold the protein result in triple disruptions that allows rapid identification and elimination from subsequent screening. This technology was applied to the signaling hub protein Fis1, which is involved in mitochondrial fission, and its interactions with itself, Dnm1, and Mdv1.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the terms "interacting" or "interaction" means that two protein fragments, domains or complete proteins exhibit sufficient physical affinity to each other so as to bring the two "interacting" protein domains or proteins physically close to each other. An extreme case of interaction is the formation of a chemical bond that results in continual and stable proximity of the two domains or proteins. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, Van der Waals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between a hub protein and a spoke protein, antigen and antibody, ligand and receptor, enzyme and substrate, and the like. In a specific embodiment, a mutant target protein (e.g., a hub protein) may bind with an interacting partner.

An "interaction" between two protein domains or complete proteins (e.g., a hub protein and one or more interacting partners) can be determined by a number of methods. For example, an interaction can be determined by functional assays such as the two-hybrid system. Protein-protein interactions can also be determined by various biochemical approaches based on the affinity binding between two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art.

A "target protein" is a protein to be studied using the methods of the present invention. Typically, a target protein is a protein involved in signaling networks. In certain embodiments, a target protein is a centrally-located hub protein that controls the integration of multiple signals into a single response. As described herein, one such protein is Fis1, mitochondrial dynamics protein that regulates mitochondrial morphology through interaction with at least 3 proteins. A target protein interacts with multiple interacting partners. In specific embodiments, a target protein interacts with at least two interacting partners. A target protein can interact with about 2, about 3, about 4, about 5, about 6, about 7, about 8, about 9, about 10 or more interacting partners. The present invention contemplates studying the interaction of a target protein with "N" interacting partners where N equals any number greater than 2. In particular embodiments, and as described herein, a library of mutant target proteins is generated using techniques known in the art (e.g., error prone PCR). This library of mutant target proteins can be screened against N number of interacting partners and amino acids of critical to protein-protein interactions can be identified and studied further.

The terms "fusion protein," "fusion polypeptide," "fusion peptide," "hybrid protein," "hybrid polypeptide," and "hybrid peptide" are used herein interchangeably to mean a non-naturally occurring protein having a specified polypeptide molecule covalently linked to one or more polypeptide molecules that are not naturally linked to the specified polypeptide. Thus, for example, a "fusion protein" may be two naturally occurring proteins or fragments (hereof linked together by a covalent linkage. A "fusion protein" may also be a protein formed by covalently linking two artificial polypeptides together. Typically but not necessarily, the two or more polypeptide molecules are "fused" together by a peptide bond, or linked indirectly via a linker moiety, forming a single non-branched polypeptide chain. In particular embodiments, a mutant target protein (e.g., a hub protein) is fused to a DNA binding domain of a transcription factor. In other embodiments, a mutant target protein (e.g., a hub protein) is fused to an activation domain of a transcription factor. In other embodiments, an interacting partner is fused to a DNA binding domain or an activation domain of a transcription factor. In more specific embodiments, N number of interacting partners are each fused to an activation domain of a transcription factor and a library of mutant target proteins (which interact with N number of interacting partners) are each fused to a DNA binding domain of the transcription factor in a two-hybrid system. The number of interacting partners may vary depending on the protein network being studied. Indeed, "N" could be an entire interactome of a hub protein.

The term "chimeric gene" refers to a non-naturally occurring nucleic acid having covalently linked together two or more distinct portions that are not naturally linked directly to each other. Each "chimeric gene" encodes a fusion protein. In specific embodiments, a chimeric gene encodes a fusion protein comprising a mutant target protein fused to either a DNA binding domain or an activation domain of a transcription factor. In other embodiments, a chimeric gene encodes a fusion protein comprising an interacting partner fused to either a DNA binding domain or an activation domain of a transcription factor.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter. In the present invention, expression vector include chimeric genes encoding fusion proteins described herein.

II. Yeast Two-Hybrid System

A "yeast two-hybrid assay" or "yeast two-hybrid system" are used interchangeably herein and refer to an assay or system for the detection of interactions between protein pairs. In a typical two-hybrid screening assay/system, a transcription factor is split into two separate fragments, the binding domain (BD) and the activation domain (AD), each of which are provided on separate plasmids, and each of which is fused to a protein of interest. The yeast two-hybrid assay system comprises (i) a "bait" vector, comprising a bait protein and the BD of the transcription factor utilized in the system; (ii) a "prey" vector, comprising a prey protein (or a library of prey proteins to be screened for interaction with the bait protein) and the AD of the transcription factor; (iii) a suitable reporter yeast strain containing the activation sequence for the transcription factor used in the system, which drives the expression of one or more reporter proteins. The bait and prey vectors are introduced into the reporter yeast strain, wherein the expressed bait and prey proteins may interact. Alternatively, separate haploid yeast strains each containing either a bait vector or a prey vector can be mated and the resulting diploid yeast strain expresses both proteins. Interacting bait and prey protein pairs result in the reconstitution and activation of the transcription factor, which then binds to its compatible activation domain provided in the reporter yeast strain, which in turn triggers the expression of the reporter gene, which may then be detected.

Any yeast cell can be used in the methods of the present invention. In particular embodiments, haploid cells of a yeast species within the genus of *Saccharomyces*, particularly *Saccharomyces cerevisiae*, are used. Other examples of suitable yeast species include, but are not limited to, *Hansenula polymorpha, Pichia pastoris*, and *Schizosaccharomyces pombe*. Indeed, numerous yeast strains or derivative strains are known in the art. Many of them have been developed specifically for certain yeast two-hybrid systems. The application and optional modification of such strains for purposes of the present invention should be apparent to a skilled artisan apprised of the present disclosure. Methods for genetically manipulating yeast strains using genetic crossing or recombinant mutagenesis are well known in the art. See, e.g., Rothstein, 101 METH, ENZYMOL., 202-11 (1983). Yeast strains that can be used in the present invention include, but are not limited to, L40, EGY48, and MaV103. Such strains are generally available in the research community, and can also be obtained by simple yeast genetic manipulation. See generally. THE YEAST TWO-HYBRID SYSTEM, Bartel and Fields, eds., pages 173-182, Oxford University Press, New York, N.Y., 1997; Kumar et al., 272 J. BIOL CHEM. 13548-13554 (1997); and Vidal et al., 93 PROC NATL. ACAD. SCI. USA, 10315-10320 (1996). In addition, the following yeast two hybrid kits are commercially available Proquest™

(Invitrogen Corp., Carlsbad, Calif.); Matchmaker Gold (Clontech Laboratories, Inc., Mountain View, Calif.); DUALhybrid (DualSystems Biotech AG, Switzerland); and HybriZAP 2.1 (Agilent Technologies, Inc., Santa Clara, Calif.).

In several embodiments, haploid yeast strains containing a vector expressing a target protein are mated with haploid yeast strains containing a vector expressing an interacting partner. The genetic basis of yeast mating control is well understood in the art. See e.g., Herskowitz et al., in The Molecular and Cellular Biology of the Yeast *Saccharomyces*: Gene Expression, Vol. 11, Jones et al., Ed., Cold Spring Harbor Laboratory Press, Cold Spring Harbor, N.Y., 1992. Essentially, yeast have two haploid mating types, a and alpha. Haploid cells of a-mating type mate with cells of alpha-mating type to form a/alpha cells. Mating can be conducted in any known methods in the art. For example, yeast strains to be mated can be mixed in a liquid medium or on a solid medium (e.g., agar plate) to allow the a-mating type cells to be in contact with the alpha-mating type cells. In specific embodiments, mating is conducted in a relatively rich medium for a sufficient time, e.g., one hour to overnight. Selection pressure can be imposed on the yeast cells at the time of mating or after mating is completed.

To express the fusion proteins in yeast cells of the present invention, chimeric genes encoding the fusion proteins may be introduced into the yeast cell by any suitable methods known in the art. Preferably, the chimeric genes are carried in an expression vector. Each chimeric gene can be included in a separate expression vector, e.g., one expression vector carries a chimeric gene that encodes a hub protein and a second expression vector carries a chimeric gene that encodes an interacting partner. Alternatively, the two chimeric genes encoding the two fusion proteins can be included in the same expression vector. The chimeric genes may have a constitutive promoter to allow constitutive expression of the chimeric genes to produce the fusion proteins. Inducible or repressible promoters may also be used such that the expression of the fusion proteins can be easily controlled. Also, the expression vectors carrying one or more chimeric genes can be maintained in the yeast cell as self-replicating extra-chromosomal elements or stably integrated into a host chromosome.

The expression of recombinant proteins in yeast is a well developed area, and the techniques useful in this respect are disclosed in detail in THE MOLECULAR BIOLOGY OF THE YEAST SACCHAROMYCES, Eds. Strathern et al., Vols. I and II, Cold Spring Harbor Press, 1982; Ausubel et al., CURRENT PROTOCOLS IN MOLECULAR BIOLOGY, New York, Wiley, 1994; and Guthrie and Fink, GUIDE TO YEAST GENETICS AND MOLECULAR BIOLOGY, in METHODS IN ENZYMOLOGY, Vol. 194, 1991, all of which are incorporated herein by reference. Sudbery, 7 CURR. OPIN. BIOTECH. 517-524 (1996) reviews the success in the art in expressing recombinant proteins in various yeast species; the entire content and references cited therein are incorporated herein by reference. In addition, Bartel and Fields, eds., THE YEAST TWO-HYBRID SYSTEM, Oxford University Press, New York, N.Y., 1997 contains extensive discussions of recombinant expression of fusion proteins in yeast in connection with various yeast two-hybrid systems, and cites numerous relevant references. These and other methods known in the art can all be used for purposes of the present invention. The application of such methods to the present invention should be apparent to a skilled artisan apprised of the present disclosure.

Generally, the vectors for recombinant expression in yeast include a yeast replication origin such as the 2μ origin or the ARSH4 sequence for the replication and maintenance of the vectors in yeast cells. In certain embodiments, the vectors also have a bacteria origin of replication (e.g., ColE1) and a bacteria selection marker (e.g., $amp^R$ marker). Optionally, the CEN6 centromeric sequence is included to control the replication of the vectors in yeast cells.

Any constitutive or inducible promoters capable of driving gene transcription in yeast cells may be employed to control the expression of the chimeric genes. Such promoters are operably linked to the coding region of the chimeric genes. Examples of suitable constitutive promoters include, but are not limited to, the yeast ADH1, PGK1, TEF2, GPD1, HIS3, and CYC1 promoters. Examples of suitable inducible promoters include but are not limited to the yeast GAL1 (inducible by galactose), CUP1 (inducible by $Cu^{++}$), MEL1 (inducible by galactose), FUS1 (inducible by pheromone) promoters; the AOX/MOX promoter from *H. polymorpha* and *P. Pastoris* (repressed by glucose or ethanol and induced by methanol); chimeric promoters such as those that contain LexA operators (inducible by LexA-containing transcription factors); and the like, inducible promoters are preferred when the fusion proteins encoded by the chimeric genes are potentially toxic to the host cells.

As discussed above, in the various embodiments of the present invention, the reporter gene contains a promoter responsive to a transcriptional activator reconstituted from the DNA binding domain and transcriptional activation domain in the fusion proteins. Any transcriptional elements known in the art may be used so long as they confer on the reporter gene the ability to respond to a transcriptional activator or repressor reconstituted or released as a result of the interaction between two test polypeptides in the fusion proteins expressed. Various transcription factors useful in yeast two-hybrid systems have been described and/or are commercially available, including without limitation GAL4, GCN4, ARD1, the human estrogen receptor, *E. coli* LexA and B42 proteins, herpes simplex virus VP16, NF-kB p65, and the like. In addition, hybrid transcriptional activators composed of a DNA binding domain from one transcriptional activator and an activation domain from another transcriptional activator are also known.

In particular embodiments, a transcriptional termination signal is operably linked to the chimeric genes or the reporter genes in the expression vectors. Generally, transcriptional termination signal sequences derived from, e.g., the CYC1 and ADH1 genes can be used. Termination sequences such as the polyadenylation signals derived from bovine growth hormone gene, SV40, lacZ and AcMNPV polyhedral genes may also be operably linked to the chimeric genes.

In addition, an epitope tag coding sequence for detection and/or purification of the fusion proteins can also be incorporated into the expression vectors. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. In addition, nucleic acid sequences encoding nuclear localization signals may also be included in a chimeric gene if it is desirable for the fusion protein encoded by the chimeric gene to be localized in cell nucleus.

Additionally, in particular embodiments, the expression vectors contain one or more selecting markers for the selection and maintenance of only those yeast cells that harbor the chimeric genes. Any selectable markers known in the art can be used for purposes of this invention so long as yeast cells expressing the chimeric gene(s) and/or reporter genes of the present invention can be positively identified or negatively selected. Examples of markers that can be positively identified are those based on color assays, including the lacZ gene which encodes β-galactosidase, the firefly luciferase gene, secreted alkaline phosphatase, horseradish peroxidase, the blue fluorescent protein (BFP), and the green fluorescent protein (GFP) gene. Other markers emitting fluorescence, chemiluminescence, UV absorption, infrared radiation, and the like can also be used. Among the markers that can be selected are auxotrophic markers that include, but are not limited to, URA3, HIS3, TRP1, LUE2, LYS2, ADE2, and the like. Typically, for purposes of auxotrophic selection, the yeast host cells containing the bait vector and/or prey vector are cultured in a medium lacking a particular nutrient. Other selectable markers are not based on auxotrophies, but rather on resistance or sensitivity to an antibiotic or other xenobiotic. Examples include, but are not limited to, chloramphenicol acetyl transferase (CAT) gene, which confers resistance to chloramphenicol; CAN1 gene, which encodes an arginine permease and thereby renders cells sensitive to canavanine; the bacterial kanamycin resistance gene ($kan^R$), which renders eucaryotic cells resistant to the aminoglycoside G418; and CYH2 gene, which confers sensitivity to cycloheximide. In addition, the CUP1 gene, which encodes metallothionein and thereby confers resistance to copper, is also a suitable selection marker. Each of the above selection markers may be used alone or in combination. One or more selection markers can be included in a particular expression vector. As will be apparent, the selection markers used should complement the host strains in which the expression vectors are expressed. In other words, when a gene is used as a selection marker gene, a yeast strain lacking the selection marker gene (or having mutation in the corresponding gene) should be used as haploid host cells to make yeast haploid cells.

In specific embodiments, auxotrophic markers such as URA3, HIS3, TRP1, LEU2, LYS2, ADE2 and the like are used. Thus, for example, a haploid yeast cell of a-mating type expressing, a mutant target protein may be defective in its URA3 gene (Ura$^-$) and cannot grow in a medium lacking uracil. However, the haploid yeast cell has a functional HIS3 gene (His$^+$). A haploid cell of alpha-mating type expressing an interacting partner has a functional URA3 gene (Ura$^+$) but is defective in HIS3 (His$^-$) and cannot grow on a His$^-$ medium. Thus, on a medium lacking both histidine and uracil, neither haploid cell can grow. Only diploid cells resulting from mating between the haploid yeast cells can form colonies.

In another embodiment, antibiotics resistance can be used as reporting markers. For example, a haploid yeast cell of a-mating type expressing a mutant target protein may have a chloramphenicol acetyl transferase (CAT) gene, which confers resistance to chloramphenicol, but does not express the bacterial kanamycin resistance gene ($kan^R$), which is required for resistance to the aminoglycoside G418. In contrast, a haploid cell of alpha-mating type expressing an interacting partner may express the kanamycin resistance gene but not the CAT gene. By co-culturing the two cells in a medium containing both chloramphenicol and G418 under conditions conducive to mating, the haploid cells will not grow and only a diploid cell resulting from mating can propagate.

In addition, as described throughout, mutants of the target protein (e.g., a hub protein) are generated and used in the two-hybrid system to identify which amino acids are involved in protein-protein interactions. In this respect, various mutations can be introduced into the target protein and the effect of the mutations on protein-protein interaction is examined by the above-discussed detection method. Various mutations including amino acid substitutions, deletions and insertions can be introduced into a protein sequence using conventional recombinant DNA technologies. In particular embodiments, a library of mutant target proteins can be generated using error prone PCR. As described in the Examples, the present invention is designed such that disruptions of the two-hybrid interaction that result from frameshift mutations, premature stop codons, mutations that unfold the target protein or other mutations not relevant to a disruption of the protein-protein interaction, are easily identified and removed from further screening.

Although the foregoing description of two-hybrid systems is described in the context of yeast, it is understood that the disclosure is not so limiting and that the present invention is applicable to other types of two-hybrid systems including mammalian and bacterial systems. Such systems are well known in the art and are commercially available. For example, mammalian two-hybrid systems and kits include, but are not limited to, Mammalian Matchmaker™ (Catalog No. 630301) (Clonetech Laboratories, Inc., Mountain View, Calif.); Mammalian Two-Hybrid Assay Kit (Catalog No. 211344) (Agilent Technologies, Inc., Santa Clara, Calif.); and CheckMate™ Mammalian Two-Hybrid System (Product No. E2440) (Promega Corp., Madison, Wis.) In addition, the present invention contemplates not only the use of the mating based yeast two-hybrid system, but also co-transformation of yeast as well as mammalian and bacterial systems.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Plasmid Construction.

For pGADT7-Fis1ΔTM, pGADT7-ΔN$_{16}$Fis1ΔTM, pBHA-Fis1ΔTM, and pBHA-ΔN$_{16}$Fis1ΔTM, Fis1ΔTM or ΔN$_{16}$Fis1ΔTM were PCR amplified using Pfu Turbo DNA polymerase (Agilent Stratagene, La Jolla, Calif.) from pET29b-Fis1 (Wells et al., 282 J. BIOL. CHEM. 33769-75

(2007)) as EcoRI/BamHI fragments and were subcloned into the pGADT7 and pBHA yeast two hybrid vectors (vectors gift of Dr. Craig Blackstone, NIH/NINDS). Dnm1 was amplified from pMAL-Dnm1 (Wells et al., 2007) as an NdeI/BamHI fragment to generate pGADT7-Dnm1 or as a SmaI/SalI fragment to generate pBHA-Dnm1. DNA encoding the full-length Mdv1 protein was cloned into pBHA and pGADT7 as an EcoRI/BamHI fragment. pGAL-Fis1 was generated from pGALGFP-Fis1 (gift of Dr. Marie Hardwick, Johns Hopkins School of Public Health), by PCR amplification, followed by cloning into XbaI and XhoI sites. For pRS416-MET25-9MycFis1, the MET25-9MycFis1 fragment was removed from pRS415-MET25-9MycFis1 (gift of Dr. Janet Shaw, University of Utah) with SacI and XhoI and subcloned into pRS416 (gift of Dr. Janet Shaw). For pRS415-MET25-3HAMdv1, the 3HA cassette was first removed from pRS426-Dnm13HA (gift of Dr. Janet Shaw) as a NotI/SpeI fragment, and subcloned into pRS415. To generate pRS415-MET25-3HAFis1, the 3HA cassette was then removed from pRS415 as a NotI/HindIII fragment and subcloned into pRS415-MET25-9MycFis1, after the 9Myc cassette had been removed by digestion with NotI and HindIII. Finally, to generate pRS415-MET25-3HAMdv1, Mdv1 was removed from pRS415-MET25-GFP-Mdv1 (gift of Dr. Janet Shaw) as a BamHI/XhoI fragment and subcloned into pRS415-MET25-3HAFis1, after Fis1 had been removed by digestion with BamHI and XhoI. Fis1 single point mutations were introduced into pGAL-Fis1 and pRS416-MET25-9MycFis1 using the QuikChange method (Agilent Stratagene). All constructs were verified by DNA sequencing.

Non-Mating Based Yeast Two-Hybrid Assays.

The yeast L40a strain (MATα, trp1, leu2, his3, LYS::lexA-HIS3, URA3::lexA-LacZ, gift of Dr. David Zappulla, Johns Hopkins University) was used to perform the yeast two-hybrid experiment shown in FIG. 7. Cells transformed with the indicated bait and prey constructs were grown overnight in -Leu/Trp selective media (MP Biomedicals, Solon, Ohio), collected by centrifugation, resuspended in water at a concentration of 1 $OD_{600}$/ml and subjected to 10-fold serial dilutions in water. Growth of transformants on -His/Leu/Trp selective media (MP Biomedicals), supplemented with 5-25 mM 3-amino-1,2,4-triazole (Sigma-Aldrich, St. Louis, Mo.) was used to measure interaction strength. Plates were photographed after incubation at 30° C. for 3 days. At least three independent experiments were performed, with similar results.

PCR Mutagenesis of $\Delta N_{16}Fis1\Delta TM$.

Error-prone PCR mutagenesis was performed according to the method of Muhlrad et al., 8 YEAST 79-82 (1992). Briefly, mutagenized $\Delta N_{16}Fis1\Delta TM$ molecules with ends homologous to pGADT7 were generated using forward and reverse primers that each contained 36-nucleotide regions of homology with the pGADT7 multi-cloning site. Mutagenic PCR was performed using Taq DNA polymerase (Invitrogen, Carlsbad, Calif.) with 0.2 µg of forward and reverse primers and 100 ng template pGADT7-$\Delta N_{16}Fis1\Delta TM$ in mutagenic buffer (50 mM KCl, 10 mM Tris-HCl, pH 8.3, 3.5 mM $MgCl_2$) in which 0.25 mM $MnCl_2$ was used and dATP was limited (200 µM dCTP, 200 dGTP, 200 µM dTTP, 20 µM dATP). PCR reaction conditions were: 95° C. for 5:00, followed by 30 cycles of 95° C. for 1:00, 59° C. for 0:45, 70° C. for 1:30, followed by a 10 minute extension hold at 72° C. The product of the PCR reaction corresponding to the molecular weight of $\Delta N_{16}Fis1\Delta TM$ was then gel purified and used for homologous recombination.

Library Construction by Homologous Recombination.

For homologous recombination, 100 ng of gel-purified pGADT7 that had been digested with EcoRI and XhoI (New England Biolabs, Ipswich, Mass.) was combined with 500 ng of gel-purified mutagenized $\Delta N_{16}Fis1\Delta TM$. This mixture was transformed into L40a yeast, and transformants were selected by growth on -Leu selective media. After 3 days, 3100 individual colonies were restruck onto fresh -Leu plates and allowed to incubate overnight at 30° C. Plates were stored at 4° C. until use.

Mating-Based Yeast Two-Hybrid Assay.

Prior to performing the mating-based assay, yeast strain AMR70α (MAαT, trp1, leu2, his3, URA3::lexA-LacZ, gift of Dr. David Zappulla) was transformed with either empty pBHA, pBHA-$\Delta N_{16}Fis1\Delta TM$, pBH-Dnm1, or pBHA-Mdv1. Transformants were selected by growth on -Trp selective media. To perform the mating-based yeast two-hybrid assay, these transformed AMR70α ("bait") strains were grown overnight at 30° C. in 15 mL of -Trp selective media. At the same time, individual colonies of L40a transformed with mutagenized pGADT7-$\Delta N_{16}Fis1\Delta TM$ ("prey") were inoculated into a 96-well plate containing 225 µL -Leu selective media and incubated at 30° C. with shaking at 200 rpm. Each plate contained one well with a positive control (pGADT7-$\Delta N_{16}Fis1\Delta TM$) and one well with a negative control (empty pGADT7).

After overnight incubation, 50 µL of prey cells were transferred into 4 new 96-well plates, 100 µL AMR70α bait strains in YPD medium at a concentration of 1 $OD_{600}$/mL were added to each 96-well plate. Cells were allowed to mate for 12 hours at 30° C. without shaking, and were then replated using a 10 µL slot-pin replica tool (V&P Scientific, San Diego, Calif.) onto -Leu/Trp and -Leu/Trp/His media containing 5-25 mM 3-amino-1,2,4-triazole. Cells were photographed after incubation at 30° C. for 3 days. To identify Fis1 mutations that resulted in disruptions, library plasmids were rescued from L40a and were sequenced.

Yeast Growth/Death Assay for Assessing Functionality of Mitochondrial Fission In Vivo.

The S. cerevisiae strain JSY5663 (MAα a fis1::HIS3 fzo1::HIS3 his3Δ200 leu2Δ1 lys2Δ-202 trp1≠63 ura3-52, gift of Dr. Janet Shaw) was transformed with pGAL-Fis1, pGAL-Fis1 point mutants, and pGAL-$\Delta N_{16}Fis1$. Cells were grown overnight in selective media (containing dextrose), collected by centrifugation, resuspended to a concentration of 1 $OD_{600}$/ml and subjected to 10-fold serial dilutions in water. Cells were plated onto YP+Dextrose as a growth control and YP+Glycerol to select for restoration of functional mitochondrial fission as described (Hermann et al., 143 J. CELL BIOL. 359-73 (1998), Sesaki, H. & Jensen, R. E., 147 J. CELL BIOL. 699-706 (1999)). Plates were photographed after incubation at 30° C. for 5 days. Two independent experiments were performed, with similar results.

Co Immunoprecipitation (Co-IP) Assays.

Co-IP assays were performed in the wild-type yeast strain JSY5740 (MATa ura3-52 leu2Δ1 his3Δ200 trp1 Δ63, gift of Dr. Janet Shaw) transformed with pRS416-MET25-9Myc-Fis1 or point mutants and pRS415-MET25-3HA-Mdv1. Strains were grown at 30° C. in selective media to a density of 0.7-1.0 $OD_{600}$/ml, washed, resuspended in medium lacking methionine, and grown at 37° C. for 2 hours. A total of 50 $OD_{600}$ units of cells were collected, and mitochondria were isolated as described previously (Zinser, E. & Daum, G. 11 YEAST 493-536 (1995)). After isolation, mitochondria were solubilized for 1 hour at 4° C. in 400 µL IP buffer (30 mM HEPES-KOH, pH 7.4, 150 mM NaCl, 1% Triton X-100, 1:500 protease inhibitor cocktail [CalBioChem, La Jolla, Calif.]). After centrifugation at 12,500 g for 10 minutes, 250 µg of protein was incubated with 40 µL anti-c-Myc agarose-conjugated beads (Sigma-Aldrich, St. Louis, Mo.) for 12 hours at 4° C. Agarose beads were collected, washed three times in IP buffer, and incubated in 50 µL SDS-PAGE sample buffer lacking β-mercaptoethanol at 65° C. for 10 minutes to release bound proteins. After addition of β-mercaptoethanol and boiling, 25 µg of eluted protein was analyzed by SDS-PAGE and Western blotting with mouse monocolonal anti-Myc-HRP (9E10, Invitrogen), and rat monoclonal anti-HA (3F10, Roche Applied Science, Indianapolis, Ind.).

TCA Precipitation of Whole Cell Lysate.

Ten mL of cells in log-phase were collected by centrifugation, incubated in 240 µL of lysis buffer (10 M NaOH, 2 mM β-mercaptoethanol, 6 mg/ml PMSF) on ice for 20 minutes. After addition of 250 µL 50% tricholoracetic acid (TCA), this mixture was incubated on ice for an additional 20 minutes. After centrifugation for 10 minutes at 4° C., the pellet was resuspended in 500 µL 90% acetone, incubated at −20° C. for 30 minutes, and pelleted by centrifugation for 10 minutes at 4° C. The pellet was then resuspended in 60 µL TCA buffer (100 mM 2-(N-morpholino)ethanesulfonic acid (MES), pH 7.4, 3M urea, 1% SDS) (Lackner et al., 325 SCIENCE 874-77 (2009)) and 6.5 mg of protein was analyzed by SDS-PAGE and Western blotting.

Example 1: Simultaneous Screening for Disruption of Multiple Yeast Two-Hybrid Interactions To identify residues critical in a protein with multiple interacting partners, a mating-based yeast two-hybrid screen (Hotspot) was designed that allows simultaneous screening for mutations that disrupt yeast two-hybrid interactions between a "hub protein" (Protein A, FIG. 1) and "spoke proteins" (Proteins B, C, D, FIG. 1). In Hotspot, a pool of randomly generated Protein A molecules is used to create a library of yeast two-hybrid prey plasmids by transformation into it haploid yeast strain with mating type a by homologous recombination and gap plasmid repair (Muhlrad et al., 1992). Individual colonies containing mutant alleles of Protein A are then mated with bait strains of mating type α containing Proteins B, C, and D (FIG. 1). The resulting diploids are replated to select for disruption of yeast two-hybrid interactions simultaneously (FIG. 1). As proof of principle, the Hotspot assay was applied to the protein Fis1 involved in mitochondrial fission and its interactions with 3 partner proteins—itself, Dnm1 and Mdv1. While Hotspot is demonstrated here for three interacting partners, it can be extended for multiple interactions by increasing the number of bait strains in the mating step (FIG. 1).

Fis1 is a mitochondrial outer membrane protein that must coordinate interactions with at least 3 proteins (itself, Dnm1 and Mdv1) to promote mitochondrial fission in yeast. Each of these Fis1-mediated interactions is essential for mitochondrial fission (Mozdy et al., 151 J. CELL BIOL. 367-80 (2000), Karren et al., 171 J. CELL BIOL. 291-301 (2005), Lees et al., 423 J. MOL. BIOL. 143-58 (2012)). Consistent with previous biochemical and cell biological data (Mozdy et al., 2000, Wells et al., 2007, Suzuki et al., 280 J. BIOL. CHEM. 21444-21452 (2005)), robust yeast two-hybrid interactions is observed between Fis1 and its binding partners when the regulatory N-terminal domain (the Fis1 arm, residues 1-16) of Fis1 is removed (FIG. 7). Therefore, this strong yeast two-hybrid interaction was leveraged to map the Fis1-Fis1, Fis1-Dnm1 and Fis1-Mdv1 interaction surfaces using the Hotspot mating-based assay.

To identify Fis1 residues important for each interaction, mutant Fis1 molecules were randomly generated using error-prone PCR conditions chosen to produce 2-5 amino acid mutations in $\Delta N_{16}$Fis1$\Delta$TM. The PCR products were then gel purified according to the molecular weight of $\Delta N_{16}$Fis1$\Delta$TM to reduce the frequency of truncated products in the Fis1 mutant pool. Next, a pGADT7-$\Delta N_{16}$Fis1$\Delta$TM prey library was built in the yeast two-hybrid strain L40 (mat a) by homologous recombination/gapped plasmid repair of the $\Delta N_{16}$Fis1$\Delta$TM PCR product with pGADT7 (Mulhrad et al., 1992, Lehming et al., 1995). After transformation, each individual L40a colony represented a distinct mutant allele of pGADT7-$\Delta N_{16}$Fis1$\Delta$TM. However, a transformation of L40a with gapped pGADT7 vector and no $\Delta N_{16}$Fis1$\Delta$TM PCR product determined that approximately 6% of the library colonies contained repaired plasmids without the $\Delta N_{16}$Fis1$\Delta$TM gene. To ensure that these colonies with empty pGADT7 plasmids would not conthund interaction results. Hotspot was performed on 94 of the background colonies obtained from control transformations. After mating and replating all background colonies resulted in no growth on any of the 3 bait plates (data not shown). These triple disruptions are therefore easily identifiable in Hotspot and can be removed from subsequent screening.

Figure 2:
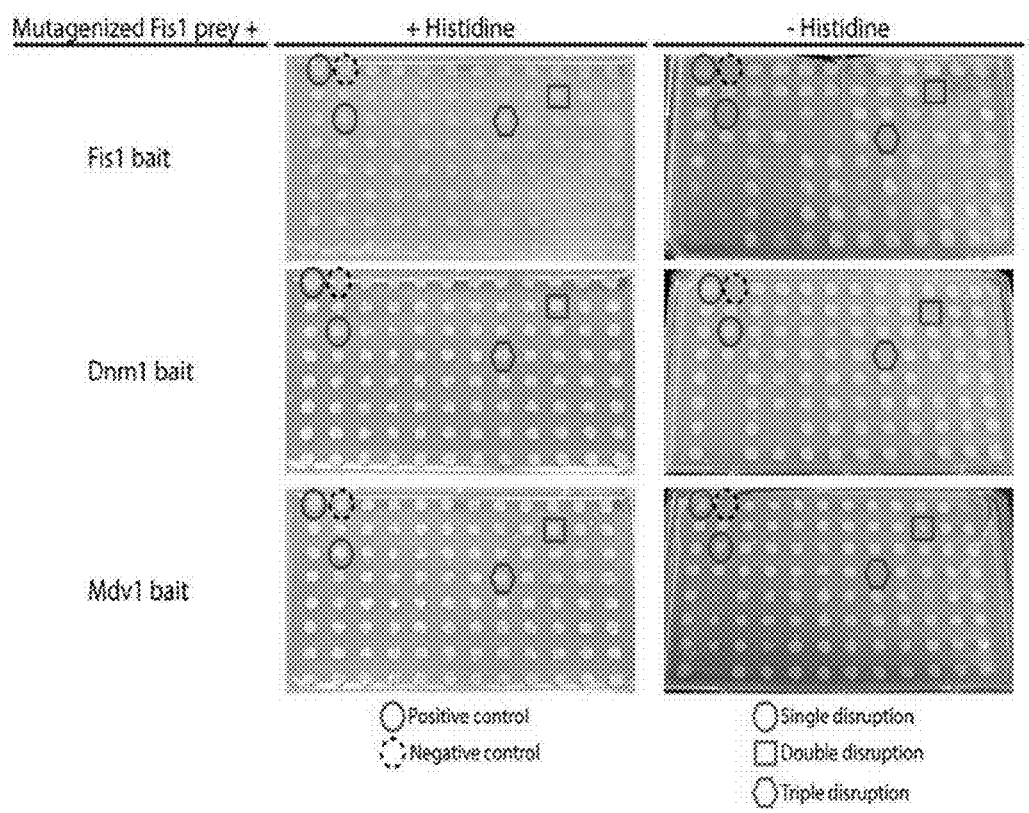
FIG. 2 shows that disruptions in the Hotspot assay are identified by colony loss on one of the three bait plates. Yeast strain L40 (Mat a) was transformed with mutagenized Fis1 prey, and single colonies were inoculated into a 96-well plate. Each plate contains a positive control (wild-type Fis1 prey, red circle), and a negative control (empty prey, black circle). After overnight incubation in selective media, cells were mated by overnight incubation in rich medium with yeast strain AMR70 (Mat α) transformed with (Top) Fis1 bait, (Middle) Dnm1 bait or (Bottom) Mdv1 bait. Cells were then replated onto media containing histidine (selection for mating) and onto media lacking histidine (selection for yeast two-hybrid interactions). Plates were photographed after incubation at 30° C. for 3 days. One example of each type of disruption is highlighted: a single disruption (blue circle), a double disruption (blue square), and a triple disruption (blue hexagon).

To perform mating-based yeast two-hybrid (FIG. 1), L40a colonies with mutagenized $\Delta N_{16}$Fis1$\Delta$TM and mated with yeast transformed with one of the haploid bait constructs in the opposite yeast two-hybrid mating strain (AMR70 mat α). The resulting diploids were simultaneously screened for the disruption of each yeast two-hybrid interaction by assessing colony loss on each of the bait plates (FIG. 2). As negative and positive controls, each 96-well plate included was one well containing empty pGADT7 prey and one well containing non-mutagenized pGADT7-$\Delta N_{16}$Fis1$\Delta$TM, respectively (FIG. 2). Cells were then replated onto media containing histidine to select for mating and onto media lacking histidine to select for yeast two-hybrid interactions. When compared to control plates, colony loss on only one bait plate signified a single disruption, double disruptions were identified by colony loss on two bait plates, and triple disruptions were characterized by colony loss on all bait plates (FIG. 2).

Figure 8:
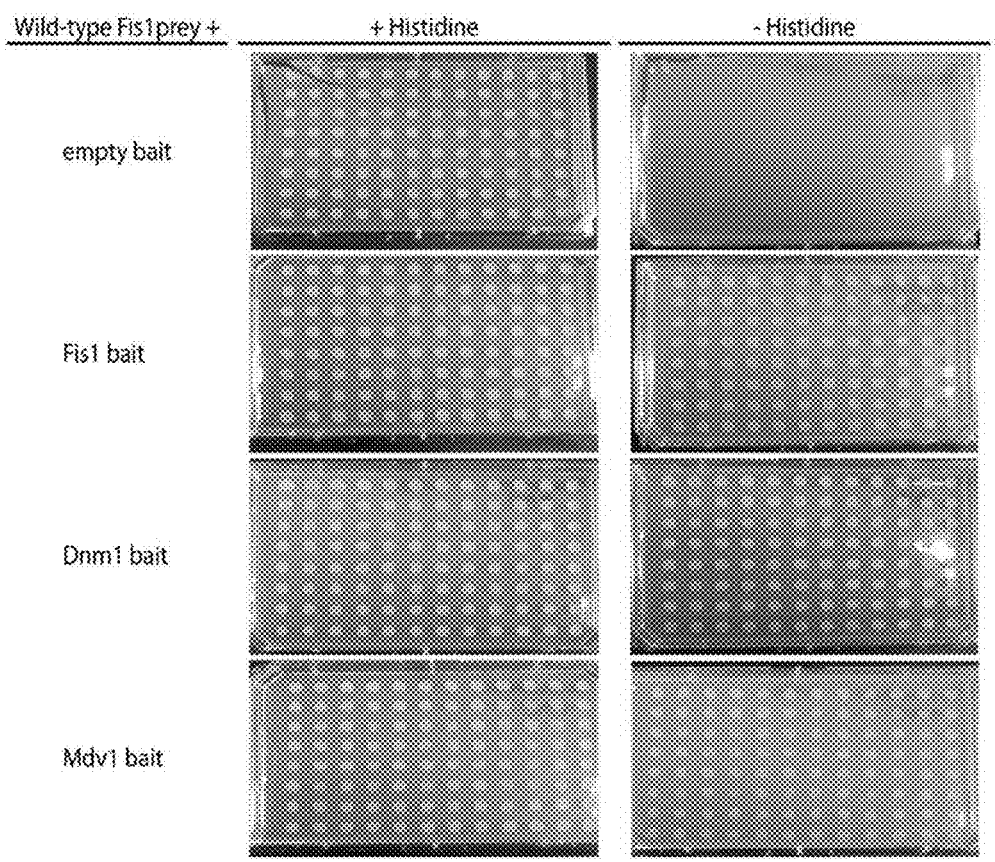
FIG. 8 demonstrates that colony loss in the yeast two-hybrid mating assay is not due to lack of mating or inefficient spotting. L40 (Mat a) transformed with non-mutagenized Fis1 prey was inoculated into each well of a 96-well plate. After overnight incubation, cells were mated with AMR70 (Mat α) transformed with (A) empty bait (B) Fis1 bait (C) Dnm1 bait or (D) Mdv1 bait. Cells were mated and spotted as above.

In Hotspot, mating ensures proper bait-prey plasmid transfer, and the subsequent replating allows for selection of disruptive interactions simultaneously. However, colony loss on one or more plate could be due to lack of mating or inefficient replating rather than loss of the yeast two-hybrid interaction. To assess this possibility, several control Hotspot assays were performed in which wild-type $\Delta N_{16}$Fis1$\Delta$TM prey was inoculated into each well of the 96-well plate (FIG. 8). After mating and replating, we found that all of the colonies grew evenly and reproducibly on all bait plates (FIG. 8). Conversely, we observed no growth when cells were mated with a strain carrying an empty bait vector (FIG. 8). These control experiments were performed 10 times with similar results, suggesting that colony loss in Hotspot is due to a lack of a yeast two-hybrid interaction, and not to inefficient matins or replating.

Example 2: Identification of Fis1 Critical Residues Using Hotspot

Of the 3008 visually screened colonies. Hotspot identified a number of mutant Fis1 alleles in each of the eight possible classes of disruptions (single disruptions (3), double disruptions (2), zero disruption (1), and triple disruption (1)) (FIG. 10). Zero disruptions represented the largest class of colonies (FIG. 10, 78.7%), followed by triple disruptions (FIG. 10, 8.9%). Hotspot is designed to serve as its own internal control in two important ways. First, yeast colonies that may contain more than one mutagenized prey plasmid likely are contained in the zero disruption class, and are thus eliminated from subsequent screening. Hotspot also immediately identifies disruptions caused by trivial reasons, since frameshift mutations, premature stop codons, mutations that unfold the protein, and empty pGADT7 plasmids all result in triple disruptions, which can readily be identified and eliminated from subsequent screening. Of the 241 sequenced, 46 clones contained frameshift mutations or premature stop codons (FIG. 11). 89.1% of these clones were identified in the triple disruption class, while the frameshift mutations and truncations in the remaining classes all occurred in the last 18 nucleotides of the Fis1 gene. This analysis supports the notion that Hotspot rapidly identifies disruptions arising for trivial reasons in the form of triple disruptions.

Figure 3:
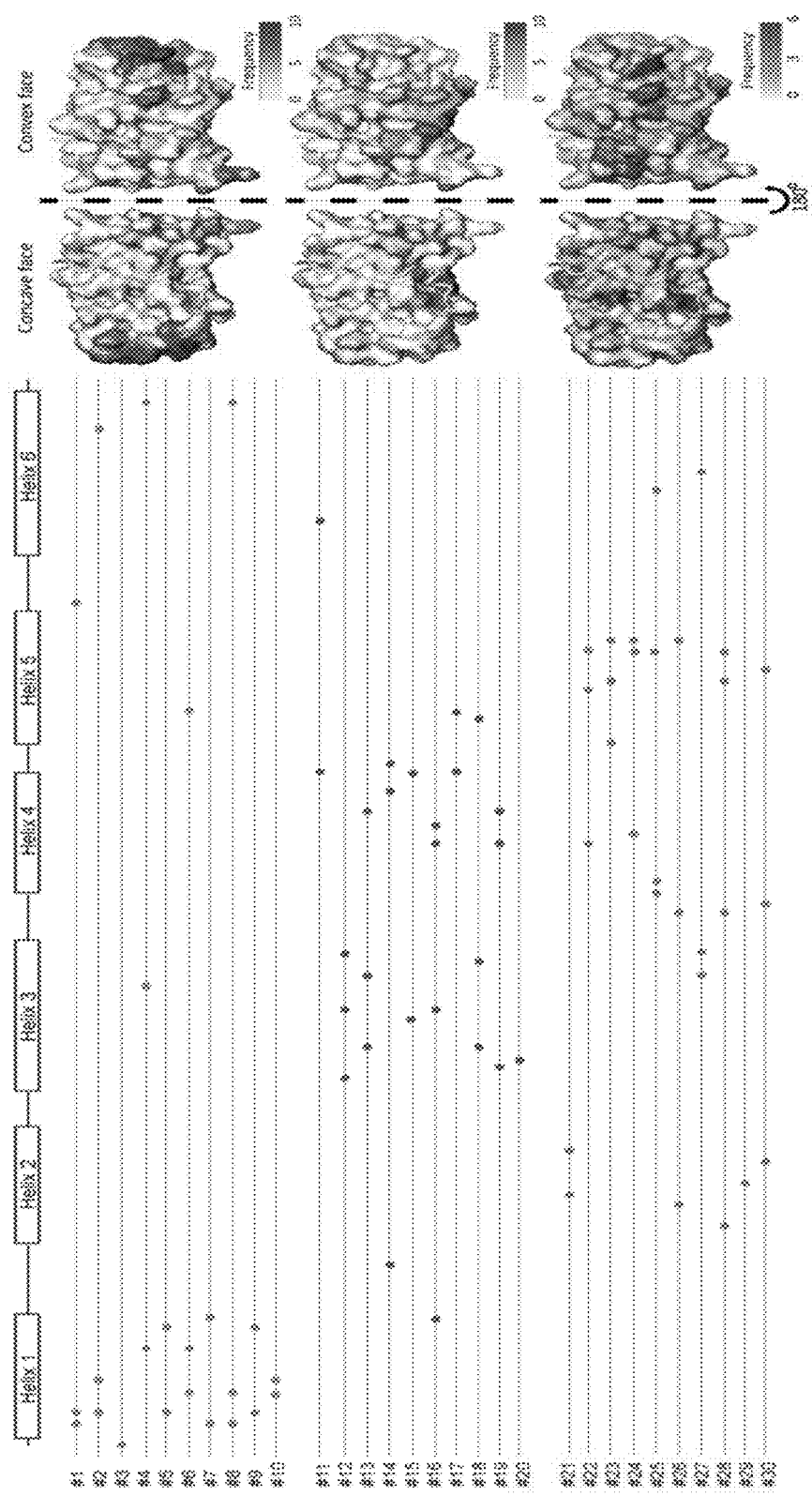
FIG. 3 is a schematic showing that application of Hotspot identities Fis1 alleles that disrupt yeast two-hybrid interactions. (Left) Schematic of a subset of Fis1 alleles that contain mutations that selectively disrupt interactions with Fis1 (top, blue), Dnm1 (middle, red), and Mdv1 (bottom, green). Each filled circle indicates a position that was mutated, interfacial residues previously inferred from biochemical and structural data are highlighted in the amino acid sequence above each section using the same color scheme. (Right) The selective disruptions identified by Hotspot are depicted on a surface representation of the Fis1 molecule (PDB entry 1y8m) for each binding partner. This figure was made in PyMol using a color gradient to indicate the frequency that an amino acid was identified in Hotspot. Surface representations incorporate all of the existing data from a total of 100 alleles identified to date.

Fis1-Fis1, Fis1-Dnm1 and Fis1-Mdv1 single disruptions constituted 3.4%, 2.9%, and 3.2% of Hotspot clones, respectively (FIG. 10). It was hypothesized that mutations that selectively disrupt Fis1-mediated interactions would affect residues at the site of that protein-protein interaction and residues affected would therefore be distinct from the other classes of selective disruptions. When the point mutations comprising the single disruptions were plotted according the amino acid sequence of Fis1, residues mutated in each class cluster in distinct regions of Fis1, with little overlap (FIG. 3). Moreover, for each class of disruptions, Hotspot identified residues previously known to be important in Fis1-mediated interactions, as well as regions not previously implicated in binding to its partners. Positions of altered residues in mutants with selectively disrupted homodimerization lie on regions that are not involved in Mdv1 or Dnm1 interaction (FIG. 3, blue circles). Fis1 residues that disrupt its interaction with Dnm1 cluster on regions known to be important in Dnm1 binding (Wells et al., 2007), and on regions not been previously implicated in Dnm1 binding (FIG. 3, red circles). Residues linked to Mdv1 binding lie on both surfaces thought important for binding Dnm1 and on part of Fis1 (helix 5) that does not mediate homodimerization or Dnm1 interactions (FIG. 3, green circles). These results suggest that Hotspot accurately and simultaneously identifies protein residues critical for binding multiple interaction partners.

Figure 4:
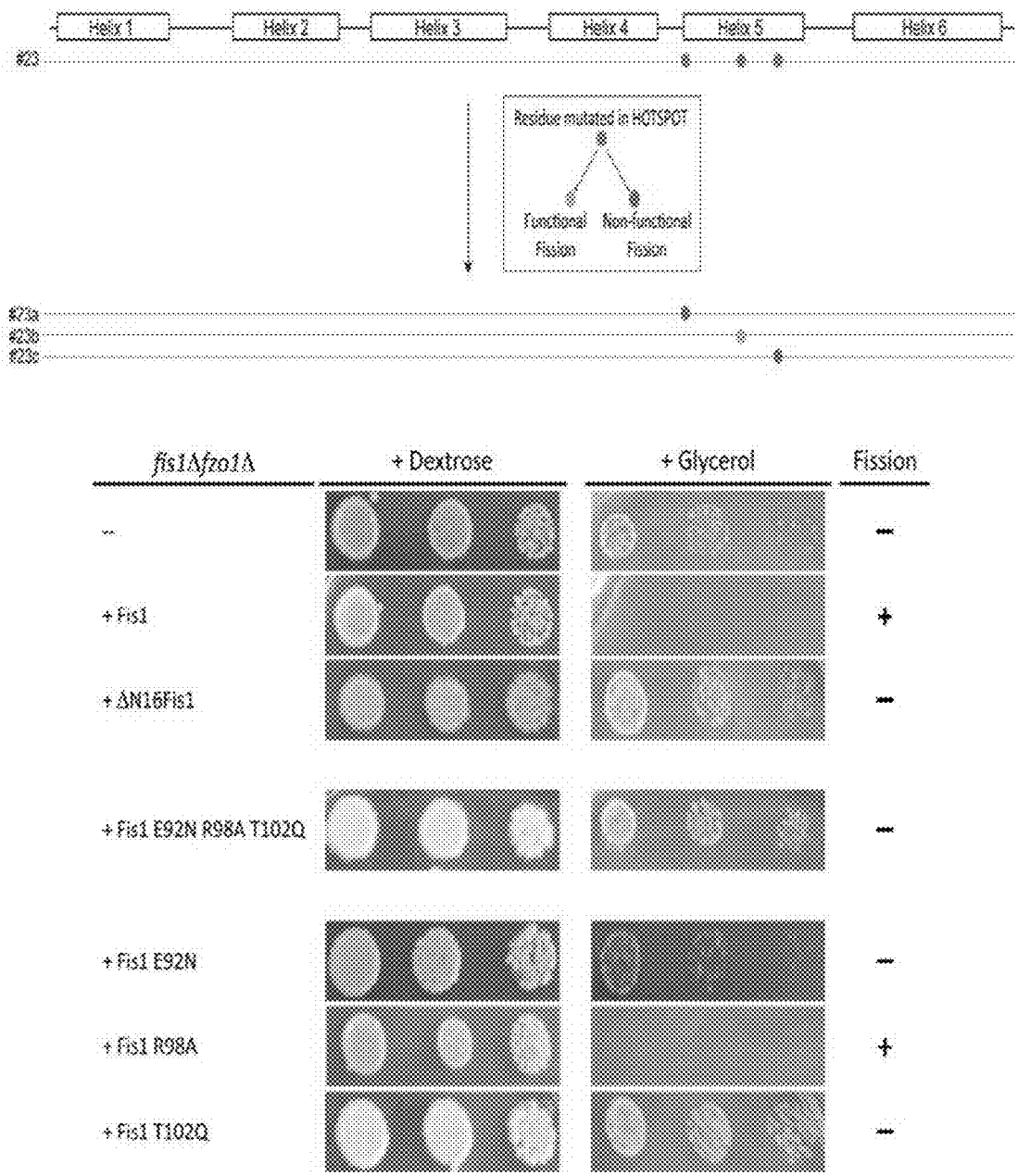
FIG. 4 demonstrates that individual Fis1 residues identified by Hotspot are essential for mitochondrial fission in vivo. (Top) Each mutant allele isolated by Hotspot as a Fis1-Mdv1 selective disruption contained 2-5 amino acid mutations per Fis1 protein. Each allele was parsed into its corresponding single point mutations for further analysis. (Bottom) Point mutations were individually subcloned into a galactose-inducible Fis1 plasmid and were tested for their ability to restore functional fission in fis1Δfzo1Δ yeast. fis1Δfzo1Δ cells are viable when grown on the non-fermentable carbon source, glycerol. If functional fission is restored, these cells have unopposed mitochondrial fission and lose their ability to metabolize glycerol from loss of mitochondrial DNA associated with excess fission. fis1Δfzo1Δ were transformed with plasmids harboring wild-type Fis1, $\Delta N_{16}$Fis1, or Fis1 single point mutations. Cells were grown overnight in selective media, collected by centrifugation, resuspended to a concentration of 1 $OD_{600}$/ml, and subjected to 10-fold serial dilutions in water. Cells were plated onto YP+Dextrose as a growth control and YP+Glycerol to select for restoration of functional mitochondrial fission. Plates were photographed after incubation at 30° C. for 5 days. Functional fission is signified by no growth on YP+Glycerol plates.

Example 3: Validation of Hotspot in a Secondary Screen for Mitochondrial Function The present approach was validated using Fis1 alleles that selectively disrupted interaction with Mdv1, since this interaction is best characterized to date (Karren et al., 2005, Zhang and Chan, 2007). It was hypothesized that Fis1 alleles identified as Fis1-Mdv1 disruptions would affect mitochondrial fission in vivo in the context of a full-length Fis1 molecule localized to the mitochondria. To test this hypothesis, Fis1 alleles were subcloned into a galactose-inducible Fis1 plasmid and were tested for their ability to restore functional mitochondrial fission in fis1Δfzo1Δ yeast. fis1Δfzo1Δ cells are viable when grown on the non-fermentable carbon source, glycerol (Hermann and Shaw, 1998, Sesaki and Jensen, 1999). If functional fission is restored, these cells have unopposed mitochondrial fission resulting in the loss of mitochondrial DNA that encodes oxidative phosphorylation proteins essential for respiration on glycerol (Hermann and Shaw, 1998, Sesaki and Jensen, 1999). Functional fission, which is observed for wild-type Fis1, is signified by no growth on YP+Glycerol plates, while non-functional fission, such as that seen in the non-functional $\Delta N_{16}Fis1$, is characterized by robust growth on YP+Glycerol plates (FIG. 4). Each of the 40 sequenced Fis1 alleles that disrupted the Fis1-Mdv1 interaction in Hotspot failed to restore fission to fis1Δfzo1Δ yeast (FIG. 4, FIG. 9). These results suggest that Fis1 alleles identified by Hotspot are important for mitochondrial fission in vivo in the context of a full-length Fis1 molecule tethered to the mitochondria.

Figure 5:
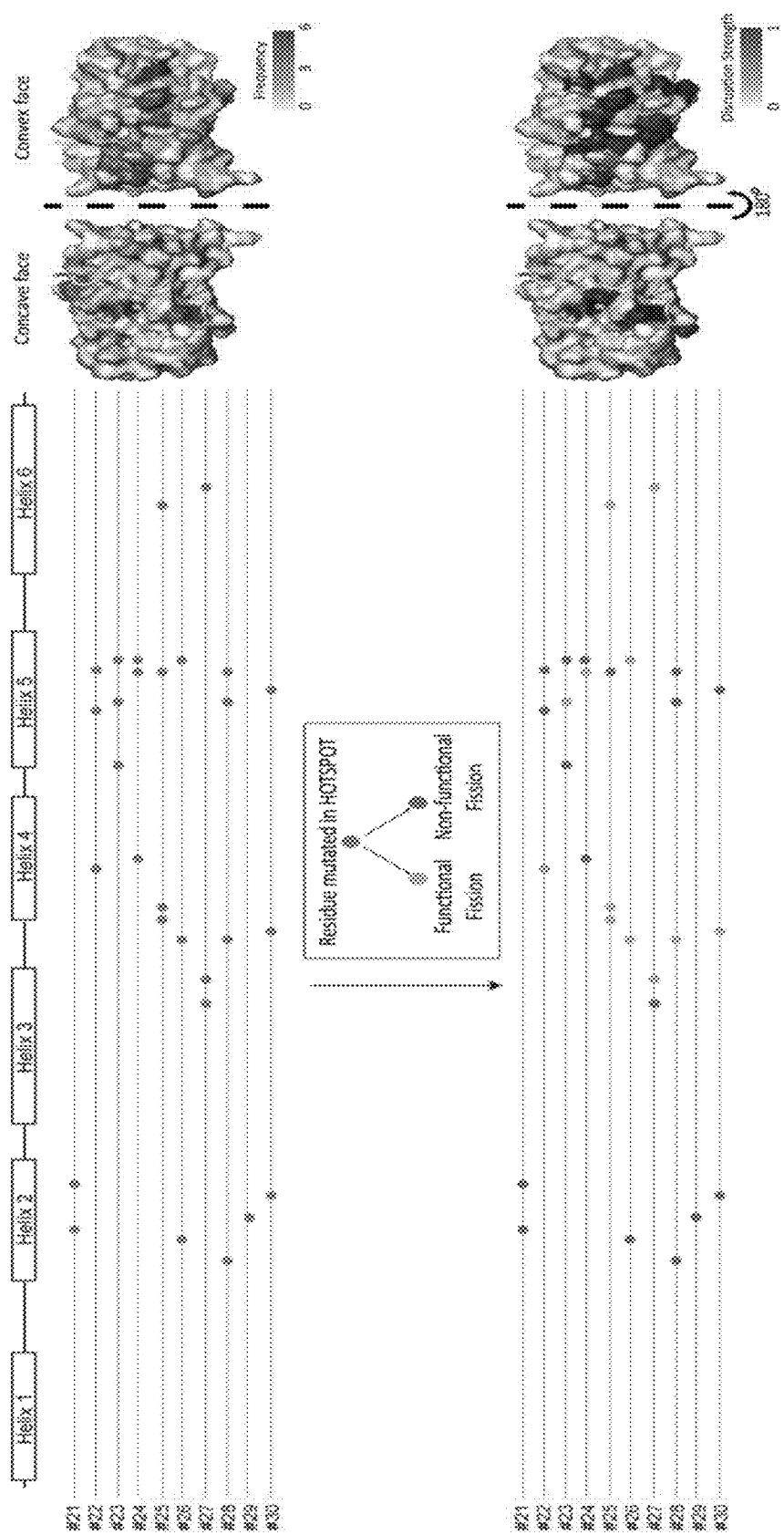
FIG. 5 shows that Hotspot identifies Fis1 alleles that involve residues not previously implicated in Fis1 interactions. (Top) Schematic representation of a subset of sequence variants identified by Hotspot with selectively disrupted Fis1-Mdv1 interactions. A surface representation of the Fis1 molecule incorporating all of the existing data from a total of 38 Fis1-Mdv1 selective disruptions is shown to the right. This figure was made in PyMOL using a color gradient to indicate the frequency that a residue was identified by Hotspot. (Bottom) Each allele was parsed into its corresponding single point mutations, which were tested individually for mitochondrial function in the yeast growth/death assay described in FIG. 4. Mutations that restored functional fission are colored gray, while mutations that resulted in nonfunctional fission are represented in dark green. Only a subset of residues from the mutant alleles is responsible for disrupting fission. These residues cluster in 2 main regions of Fis1, only one of which was previously known to be involved in Mdv1 binding. This is consistent with Hotspot reporting on an intact Fis1-Mdv1 interaction. A surface representation of Fis1 mutants that disrupted mitochondrial fission in vivo is shown to the right. Residues are colored according to disruption strength.

Each mutant allele isolated by Hotspot as a Fis1-Mdv1 selective disruption contained 1-5 amino acid mutations per $\Delta N_{16}Fis1$ protein (FIG. 10). Each of these alleles was parsed into its corresponding single point mutations and individually tested the ability of each point mutation to restore mitochondrial fission to fis1Δfzo1Δ yeast. Of the 93 individual mutations that comprised the Mdv1-selective disruptive alleles, 44 mutations were able to reconstitute functional mitochondrial fission, while 49 failed to restore fission (FIG. 4). These results suggest that a subset of Fis1 residues identified by Hotspot is important for mitochondrial fission in vivo. Moreover, these residues cluster in 2 main regions of Fis1, one of which is known to be involved in Mdv1 binding (Zhang and Chan, 2007), while the other region has not previously been thought to be important for Mdv1 binding (FIG. 5). These results are consistent with the notion that Hotspot is reporting on intact protein-protein interactions, and that Hotspot can identify novel sites of interaction between a hub protein and its effectors.

Example 4: Validation of Hotspot by Fis1-Mdv1 Co-Immunoprecipitation in Yeast

Figure 6:
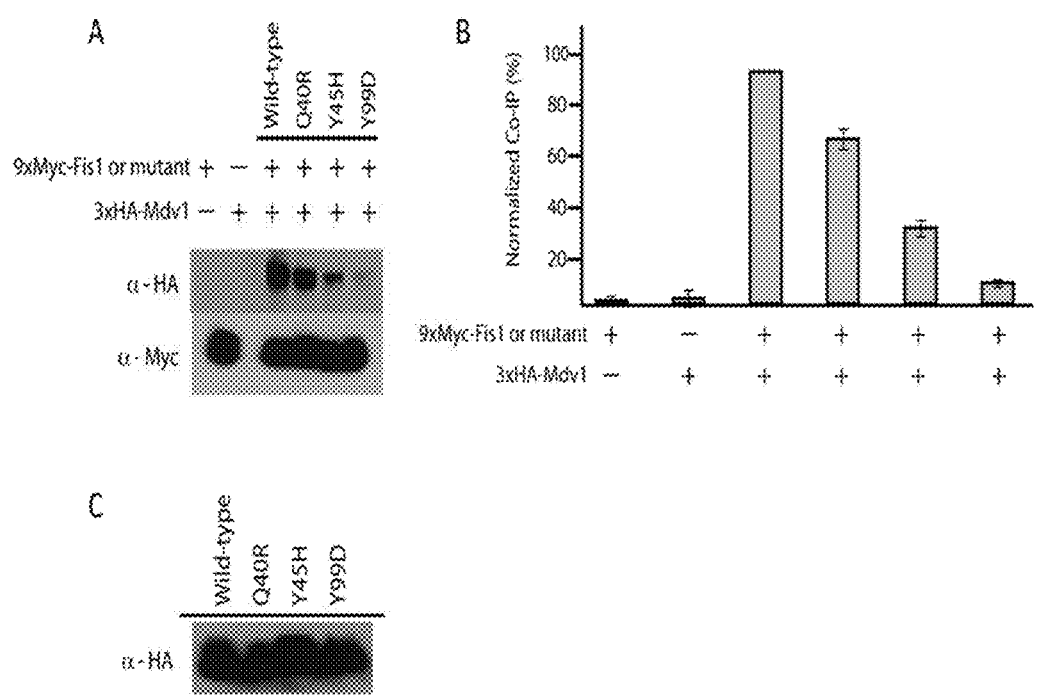
FIG. 6 illustrates that Fis1 residues identified as Mdv1 selective disruptions alter Fis1-Mdv1 interactions in vivo. A subset of Fis1 mutations that were both identified by Hotspot as Mdv1 selective disruptions and resulted in nonfunctional fission were tested for their ability to co-immunoprecipitate Mdv1 in wild-type yeast cells. 9Myc-Fis1 and 9Myc-Fis1 mutant proteins were immunoprecipitated from wild-type yeast using anti-Myc agarose-conjugated beads and the degree of 3HA-Mdv1 co-immunoprecipitation was analyzed by Western blot analysis (FIG. 6A) and quantified by densitometry (FIG. 6B). 3HA-Mdv1 co-IP levels in B were normalized to the amount of 3HA-Mdv1 present when wild-type 9Myc-Fis1 was immunoprecipitated.

The disruption of mitochondrial fission by Fis1 mutations identified in Hotspot likely arises from decreased Fis1-dependent recruitment of Mdv1 to the mitochondria. To test this idea, co-immunoprecipitation experiments were used to analyze the interaction between wild-type or mutant Fis1 proteins with Mdv1 in vivo. For these experiments, of the point mutants that failed to restore functional mitochondrial fission to fis1 Δfzo1Δ yeast, Fis1 mutations (Q40R, Y99D) were chosen that were predicted to disrupt Mdv1 binding based on crystal structure of Fis1 complexed with a peptide derived from Mdv1 (Griffin et al., 170 J. CELL BIOL. 237-48 (2005), Zhang and Chan, 2007) in addition to mutations identified here not previously thought to be important for Mdv1 binding (Y45H). Co-IP assays to test the ability of Hotspot mutations with Fis1 were performed on mitochondria isolated from wild-type yeast expressing 3HA-Mdv1 and either 9Myc-Fis1 or 9Myc-Fis1 mutants. Proteins were immunoprecipitated with anti-Myc-conjugated beads, and eluted proteins were analyzed by Western blotting with anti-HA antibodies. 9Myc-Fis1 and mutants were all effectively immunoprecipitated from solubilized mitochondria (FIG. 6A, Lanes 1, 306). As reported previously, Mdv1 co-immunoprecipitates with 9Myc-Fis1 in an antibody-dependent manner (Tieu et al., 158 J. CELL BIOL. 445-52 (2002), Karren et al., 2005, FIG. 6A, Lanes 1-3). However, less Mdv1 co-immunoprecipitated was observed when Hotspot mutations were introduced into 9Myc-Fis1 (FIG. 6A, Lanes 4-6). The Q4OR and Y99D HOTSPOT mutants, which corresponded to residues previously identified as important for Mdv1 binding, disrupted Mdv1 co-immunoprecipitation by 30% and 90%, respectively (FIG. 6B). Moreover, the HOTSPOT mutant (Y45H) not previously identified as important for Mdv1 binding, also disrupted Mdv1 co-immunoprecipitation to a similar degree as the Y99D mutant (FIG. 6B), suggesting that mutations identified by HOTSPOT are indeed important for binding Mdv1.

We claim:

1. A method for identifying a protein interaction domain of a target protein using a yeast two-hybrid system comprising the steps of:
    (a) providing a first haploid yeast cell expressing a mutant target protein fused to either an activation domain or a DNA binding domain of a transcription factor;
    (b) providing at least two haploid yeast cells of opposite mating type than the first haploid yeast cell of step (a) that express different interacting partners of the mutant target protein, wherein each interacting partner is fused to either (i) an activation domain of the transcription factor if the mutant target protein of step (a) is fused to the DNA binding domain of the transcription factor or (ii) a DNA binding domain of the transcription factor if the mutant target protein of step (a) is fused to the activation domain of the transcription factor;
    (c) mating the first haploid yeast cell of step (a) separately with each of the at least two haploid yeast cells of step (b);
    (d) replica plating the mating reactions to select for mated diploid yeast cells; and
    (e) replica plating the mating reactions to select for two-hybrid interactions, wherein a disruption of the yeast two-hybrid interaction in a selection reaction indicates that the mutated amino acids of the target protein comprise a protein interaction domain that interacts with the interacting partner expressed in the selection reaction and wherein a disruption of the two-hybrid interaction in all selection reactions that results in colony loss indicates that the disruption is likely due to a mutation that affects the stability, processing or folding of the target protein.

2. The method of claim 1, wherein steps (d) and (e) are carried out simultaneously.

3. The method of claim 1, wherein the mutant target protein comprises about 2 to about 5 amino acids that are mutated relative to the wild type target protein.

4. A method for using a yeast two-hybrid system to identify amino acid residues of a target protein that interact with interacting partners of the target protein comprising the steps of:
    (a) providing a first haploid yeast cell of mating type a that expresses a mutant target protein fused to either an activation domain or a DNA binding domain of a transcription factor;
    (b) providing N haploid yeast cells of mating type α that express N interacting partners of the mutant target protein, wherein N equals the number of interacting partners of the target protein, and wherein each interacting partner is fused to either (i) an activation domain of a transcription factor if the mutant target protein of step (a) is fused to the DNA binding domain of the transcription factor or (ii) a DNA binding domain of a transcription factor if the mutant target protein of step (a) is fused to the activation domain of the transcription factor;
    (c) mating the first haploid yeast cell separately with each of the N haploid yeast cells;
    (d) replica plating the mating reactions to select for mated diploid yeast cells; and
    (e) replica plating the mating reactions to select for two-hybrid interactions, wherein a disruption of the yeast two-hybrid interaction in a selection reaction indicates that the mutated amino acids of the target protein interact with the interacting partner expressed in the selection reaction and wherein a disruption of the two-hybrid interaction in all N selection reactions indicates that the disruption is due to a mutation not relevant to a disruption of the interaction between the target protein and the interacting partners.

* * * * *